United States Patent [19]

Sivak, Jr. et al.

[11] 4,350,148

[45] Sep. 21, 1982

[54] ESOPHAGEAL VARICES INJECTOR

[75] Inventors: Michael V. Sivak, Jr., Cleveland Heights; George J. Skipper, Chagrin Falls, both of Ohio

[73] Assignee: Cleveland Clinic Foundation, Cleveland, Ohio

[21] Appl. No.: 229,155

[22] Filed: Jan. 28, 1981

[51] Int. Cl.³ .............................................. A61B 1/00
[52] U.S. Cl. ........................................ 128/4; 128/215
[58] Field of Search ............. 128/4, 6, 218 R, 218 N, 128/221, 303 R, 215, 348, 216

[56] References Cited

U.S. PATENT DOCUMENTS

| | | | |
|---|---|---|---|
| 3,380,448 | 4/1968 | Sadove et al. | 128/215 |
| 3,659,610 | 5/1972 | Cimber | 128/215 |
| 3,830,225 | 8/1974 | Shinnick | 128/4 |
| 4,136,695 | 1/1979 | DaFoe | 128/215 |
| 4,237,871 | 12/1980 | Bonnet | 128/4 |

Primary Examiner—John D. Yasko
Attorney, Agent, or Firm—Fay & Sharpe

[57] ABSTRACT

An injector is disclosed for treating esophageal varices and other disorders with injected medications. The injector includes a needle which has a tubular bore for injecting the medication into the varices. The needle has an exposed length which is sufficiently long to enter a vein wall but not sufficiently long to pass through the vein and esophagus walls. A tubular connector has an internal bore connected with the needle and has a flange for inhibiting the connector from following the needle through a puncture. The tubular connector has a shank portion which is connected with a flexible tube. The flexible tube, tubular connector, and needle are slidingly receivable in a biopsy channel of a flexible, fiberoptic endoscope. A syringe is connected to the other end of the flexible tube for selectively forcing medications through the tube, connector, and needle into the varices.

7 Claims, 1 Drawing Figure

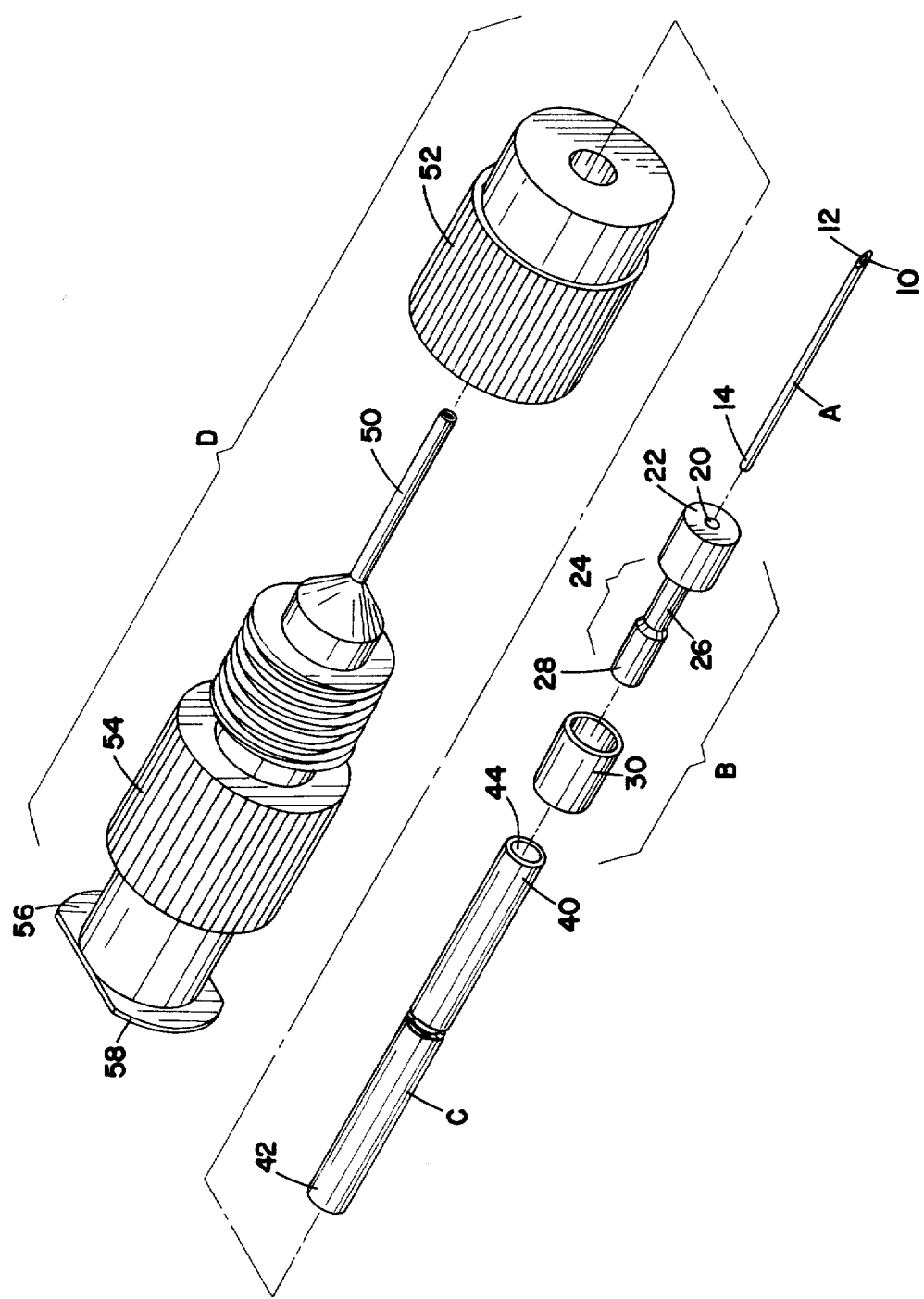

ESOPHAGEAL VARICES INJECTOR

BACKGROUND OF THE INVENTION

This application pertains to the art of non-operative esophageal treatment and more particularly to apparatus for the treatment of esophageal varices and other esophageal disorders by the injection of medications. The invention is particularly applicable to the treatment of esophageal varices in conjunction with the treatment of cirrhosis of the liver and will be described with particular reference thereto. It will be appreciated, however, that the invention has broader applications such as the treatment of esophageal disorders whose healing is promoted by a localized injection of medication.

A common side effect to cirrhosis of the liver is the development of esophageal varices. These varices are varicose venous channels which develop in the esophagus because the blood flow from the intestine to the liver is impaired by the cirrhosis. When one of these varices ruptures, life threatening internal gastrointestinal bleeding occurs. Treatment of the varices in patients with cirrhosis of the liver is hindered by the generally weakened liver condition. Many of these patients doe not have an adequate liver reserve to withstand surgery or the physiological stresses of general anesthesia.

In 1939, a procedure was described for treating the varices by injections. In this procedure, a needle was passed through a rigid endoscope and into a selected varix. Each selected varix was injected with an agent that caused scarring of the internal wall of the vein. This tended to eliminate or reduce the severity of future bleeding episodes. When this procedure was developed, endoscopes consisted of a long, rigid system of lenses housed in a long metal tube. The use of a rigid endoscope usually requires the use of a general anesthesia. This rigid endoscopic procedure was never adopted by the medical profession. Rather, operative approaches to the management of hemorrhages from esophageal varices have become the standard treatment.

Today, flexible, fiberoptic endoscopes are in common usage. The fiberoptic endoscope is a flexible tubular instrument in which light is carried in and out of the patient by bundles of glass fibers. The proximal end of the instrument i.e., the end held by the physician, has a viewing lens and controls for manipulating its opposite or distal end. The controls selectively bend the distal end causing the distal tip to be angulated in any selected direction. This allows the instrument to follow the course of the gastrointestinal tract and examine its walls. The fiberoptic endoscopes, conventionally, have a tubular biopsy channel extending from the proximal end to the distal end. Various accessories are passed through the biopsy channel into the patient's gastrointestinal tract.

It has been suggested that the 1939 injection procedure described above be adapted for use with flexible, fiberoptic endoscopes. Specifically, it has been suggested that a needle be secured to a length of flexible, plastic tubing by tying several ligatures. The flexible tubing and needle are diametrically sized to be received in the biopsy channel of conventional fiberoptic endoscopes. This procedure, however, has many drawbacks. One problem is that the rigid needle, about a centimeter in length, tends to impale the side walls of the biopsy channel. Because this construction is unsuitable for passing the needle from the proximal end to the distal end of the biopsy channel, the needle is commonly backloaded. That is, the tubing is threaded from the distal end backward through the biopsy channel to the proximal end. Another problem has been the needle becoming detached from the tubing during injections. If the needle is lengthened to enable it to be tied more securely to the tubing, the problems associated with moving the needle through the biopsy channel are compounded. Yet another problem has been the difficulty in controlling the depth of the insertion of the needle into the varix. The diameters of the tubing and the needle are so close that the tubing is readily inserted with the needle through the puncture into the varix. This tends to enlarge the puncture and cause excessive damage to the varix.

The present invention overcomes the above-referenced problems and others, yet provides an injector for non-operative treatment of esophageal varices and other esophageal disorders.

SUMMARY OF THE PRESENT INVENTION

The present invention relates to an esophageal injector which includes an elongated, flexible tube, a tubular connector, and a needle. The tubular connector is connected with the elongated, flexible tube. It has an internal bore which is connected in fluid communication with an internal passage of the flexible tube. The needle, in turn, is affixed to the connector. It has an internal bore which is connected in fluid communication with the connector bore. The flexible tube, the connector, and the needle are dimensioned to be received in a biopsy channel of a flexible, fiberoptic endoscope and to pass longitudinally through the biopsy channel from a proximal end to a distal end.

One advantage of the present invention is that it precisely controls the depth of insertion of the needle into a treated varix. The precise control eliminates the danger of inserting the needle through the varix and esophagus wall into surrounding organs.

Another advantage of the present invention is that it eliminates the possibility of the needle becoming detached during an injection and remaining embedded in a varix or the esophagus wall.

Still other advantages of the present invention will become apparent upon reading and understanding the detailed description of the preferred embodiment.

DESCRIPTION OF THE FIGURE

The invention make take physical form in certain parts and arrangements of parts. The FIGURE is for the purpose of illustrating a preferred embodiment of the invention only and is not to be construed as limiting the invention.

The FIGURE is an exploded view of an esophageal injector in accordance with the present invention.

DESCRIPTION OF THE PREFERRED EMBODIMENT

The FIGURE shows an injector for injecting medications into esophageal varices and other disorders. The injector includes a needle A for entering each varix to be treated and introducing the medication therein. The needle is connected to a tubular connector B which in turn is connected to an elongated, flexible tube C. The needle, tubular connector, and flexible tube are dimensioned to be received within a biopsy channel of a flexible, fiberoptic endoscope. More specifically, they are adapted to slide through the biopsy channel from its proximal end to its distal end even when the endoscope is disposed within the esophagus of a patient. A coupler D is connected with the flexible tube C for coupling it with a means for selectively forcing the medications through the flexible tube, the connector, and the needle into the esophageal varices.

The needle A has a sharpened end 10 for puncturing and extending through the vein walls. An internal bore 12 extends through the sharpened end 10 to inject the medications into the veins. Opposite the sharpened end 12, an end 14 is connected to the tubular connector B. In the preferred embodiment, the needle is a 25 gauge needle which is one centimeter in length.

The tubular connector B has a connector bore 20 through which the medications are conveyed. The connector bore 20 is dimensioned to receive the end 14 of the needle in a close, sliding engagement. In this manner, the connector bore and the needle bore are connected in fluid communication. The end 14 of the needle is received by the connector bore 20 until the exposed length of the needle is sufficiently long to enter the vein wall but not long enough to pass through the vein and esophagus walls. In the preferred embodiment, the exposed length of the needle is about 5 millimeters. Further to the preferred embodiment, the connector B and the needle A are affixed by soldering. However, other modes of connecting the needle and connector are contemplated including adhesive bonding, threaded engagement, and the like. Optionally, the connector bore 20 may be formed with an internal stop for limiting the sliding receipt of the needle.

The tubular connector is formed with a flange or stop 22 for inhibiting the connector from passing with the needle through the puncture in the vein wall. The flange 22 is fashioned to have a cross section which is several times that of the needle A. However, the flange is fashioned in concert with the maximum diameter of an element which may be received slidingly in the biopsy channel of the flexible, fiberoptic endoscope.

The tubular connector B has a tubular shank 24 which is dimensioned to be received in the flexible tube C. The shank 24 has a reduced diameter portion 26 which has substantially the same outer diameter as the interior diameter of the tube and an enlarged portion 28 which is received within the tube by expanding it. The shank portion 24 is inserted into the flexible tube C until the end of the flexible tube abuts the trailing face of the flange 22. A ferrule 30 is crimped around the end of the flexible tube C to increase its frictional engagement with the shank 24 of the tubular connector. More specifically, the length of the ferrule 30 is commensurate with the length of the reduced diameter portion 26. When the ferrule 30 is crimped around the end of the tube and the reduced diameter portion 26 of the connector, the enlarged portion 28 inhibits the connector from being removed from the tubing. In the preferred embodiment, the tubular connector including the ferrule 30 are machined of stainless steel. Other connector structures are contemplated by the present invention. For example, the connector may have two threadingly connected sections which cam tightly against the needle or the flexible tube.

The flexible tube C is sized to extend through the biopsy channel such that the distance between a first end 40 which is connected with the connector B and a second end 42 is longer than the length of the biopsy channel. In the preferred embodiment, the flexible tube C is about 180 centimeters. The tube has an internal passage 44 which extends the length of the tube and is dimensioned to receive the shank 24 of the tubular connector. In the preferred embodiment, the flexible tube is about 1.7 millimeters in diameter and is constructed of polyethylene or TEFLON, although other flexible materials may be used.

The coupler D is a Leur-lock fitting in which a tubular extension 50 is permanently soldered into a coupler body 52. The tubular extension is dimensioned to be received in the interior passage 44 of the tube C in a tight, frictional engagement. A compression cap 54 and the tubular extension 50 are cammed together to increase the frictional engagement with the tube C such that the second end 42 of the tube is securely locked to the coupler D. The coupler D has a pair of flanges 56 and 58 which allow the injector to be coupled with a twist motion to a Leur-lock fitting syringe or other means for selectively forcing medications through the interior passage of the flexible tube C, the connector bore 20, and the needle bore 12, into the varix.

To use the invention, a patient is sedated with an intravenous tranquilizer. A general anesthesia is unnecessary. The flexible endoscope is inserted into the patient's esophagus and its distal end is manipulated to examine the esophageal walls. If esophageal varices or other disorders which can be cured by injecting medications are observed, the end of the tube C with the attached connector B and needle A is inserted into the biopsy channel from the proximal end. They are slid through the biopsy channel until the needle is adjacent the distal end. The coupler D is connected with a syringe containing the appropriate medications. The physician operates the endoscope controls to position the distal end so that the needle is axially aligned with the esophageal varices to be treated. The tube is slid further through the biopsy channel until the needle A punctures and penetrates the vein wall and the flange 22 abuts it outer surface. The syringe is depressed to inject a measured amount of medication into the varix. After the medication is injected, the tube C is withdrawn sufficiently to remove the needle from the vein. The procedure may be repeated for additional esophageal varices. While the needle is within the vein wall, there is commonly movement of the esophagus from peristalsis, reflected motion of the heart, breathing, and small movements of the endoscope. The flexible injector allows the needle to move with the esophagus, thus reducing the chance that a sudden motion might result in tearing the varix.

The invention has been described with reference to a preferred embodiment. Obviously, modifications and alterations will occur to others upon reading and understanding this specification. It is my intention to include all such modifications and alterations insofar as they come within the scope of the appended claims or the equivalents thereof.

Having thus described in detail a preferred embodiment of my invention, I now claim my invention to be:

1. An injector comprising:
   an elongated, flexible tube having an interior passage;
   a tubular connector including a tubular shank frictionally received in the interior passage of the flexible tube, a stop for inhibiting the connector from passing through a puncture and an internal bore in fluid connection with the interior passage of the flexible tube;
   a ferrule surrounding the end of the flexible tube and the tubular connector shank, the ferrule being firmly crimped around the end of the flexible tube; and a needle affixed to the connector and having an internal bore in fluid connection with the connector bore; the flexible tube, the connector, and needle being dimensioned to be received in and slide through a biopsy channel of a flexible endoscope.

2. The injector of claim 1 wherein said stop is an annular flange.

3. The injector as set forth in claim 1 wherein the connector and needle are soldered together, whereby the needle is inhibited from becoming detached from the connector.

4. The injector as set forth in claim 1 wherein the tubular shank has an enlarged portion, the enlarged portion being received within the interior passage of the flexible tube beyond the ferrule.

5. The injector as set forth in claim 1 further including a coupler for coupling the flexible tube with a means for selectively forcing medications through the flexible tube, connector, and needle.

6. An injector for treating esophageal varices and disorders with injected medications, the injector comprising:

a needle having an internal bore through which the injected medications are conveyed;

a tubular connector including a stop for abutting the varix wall without penetrating it, a tubular shank, and an internal bore, the tubular connector being connected with the needle such that the needle has an exposed length which is sufficiently long to pass through a varix wall but not long enough to pass through the varix and esophagus walls, and the internal bores of the tubular connector and needle being in fluid communication;

an elongated, flexible tube having an internal passage, the flexible tube receiving the tubular connector shank within its internal passage such that the internal passage is connected in fluid communication with the connector bore; and, a ferrule firmly crimped around the end of the flexible tube and the tubular connector shank, the needle, tubular connector and flexible tube being slidingly receivable in a biopsy channel of a flexible, fiberoptic endoscope.

7. The injector of claim 6 wherein said stop is an annular flange.

* * * * *